Oct. 8, 1974 C. G. KLEHM Plant Pat. 3,635
PEONY PLANT
Filed Oct. 24, 1973
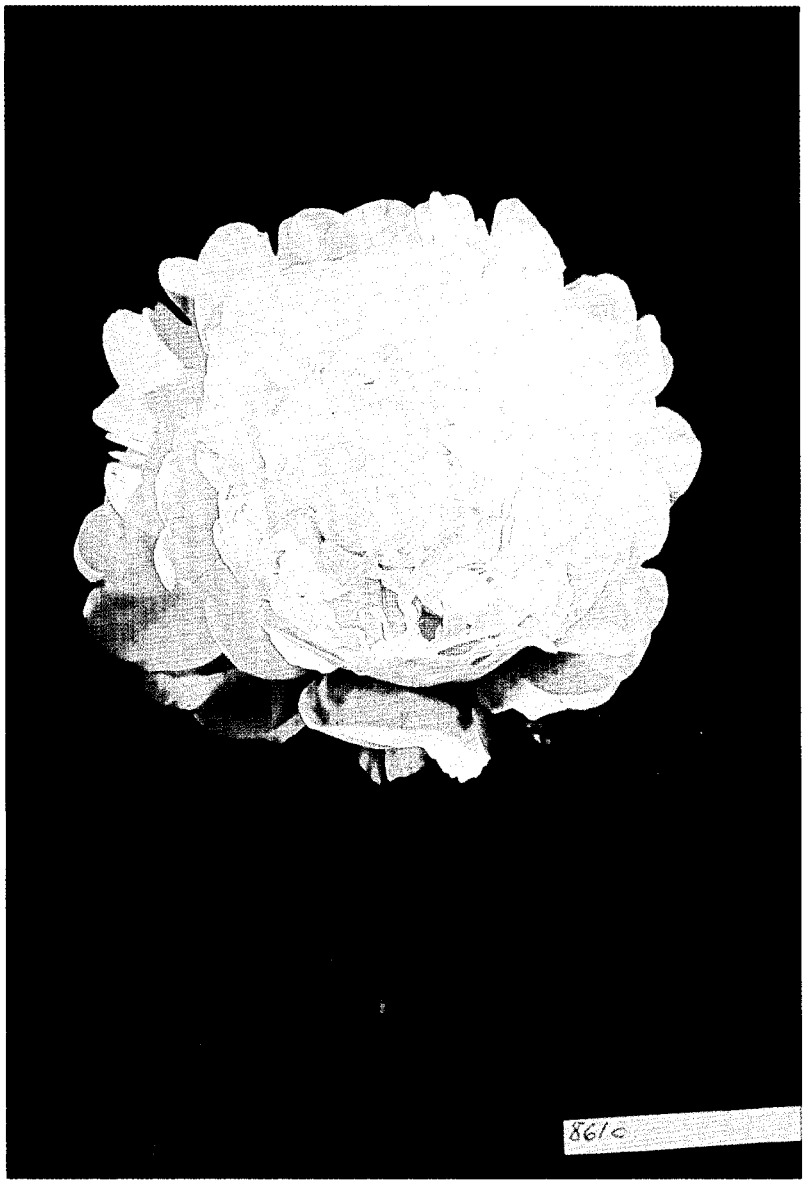

United States Patent Office

Plant Pat. 3,635

Patented Oct. 8, 1974

3,635

PEONY PLANT

Carl George Klehm, Arlington Heights, Ill., assignor to Klehm Properties, Inc., Arlington Heights, Ill.

Filed Oct. 24, 1973, Ser. No. 409,173

Int. Cl. A01h *5/00*

U.S. Cl. Plt.—68 1 Claim

ABSTRACT OF THE DISCLOSURE

A new variety of *Paeonia lactiflora* characterized by its very large, full double, rose type blossoms which have a pleasing blend of ivory and pastel pink coloring and which are carried on short, very strong stems, the plant itself being of relatively short height and having an abundance of attractive, dark green foliage.

Background of the New Plant

The herein described new variety of peony plant was originated as a seedling produced by my cross of the unpatented variety Mons. Jules Elie with an unnamed and unpatented "bull" type seedling of Mons. Jules Elie, during the course of extensive breeding efforts carried on by me at Arlington Heights, Illinois, with the objective of developing improved peony varieties, the seed parent being Mons. Jules Elie and the pollen parent being identified in my records as "variety 71D" and used specifically for hybridizing purposes.

This new plant was selected by me in 1950, from among a large number of seedlings produced by the before mentioned cross, because of the unique coloring of its blossoms and its apparent relatively short and heavily foliated, thick stemmed growth habit and extensive asexual propagation of this plant by root divisions, done by me and under my direction at Arlington Heights, Illinois, has demonstrated that the desirable and unique characteristics of the original seedling are truly conveyed from generation to generation and are firmly fixed. Commercial scale propagation of this new variety, by root divisions, is now being carried on in production farms at Arlington Heights, Barrington and Champaign, Illinois.

Description of the Drawing

My new variety of peony plant is illustrated by the accompanying photographic drawing which shows the fully opened flower in full color, the flower color shown being as nearly true as it is reasonably possible to obtain by conventional photographic procedures.

Description of the New Plant

The following is a detailed description of my new variety of peony plant with color specification according to The RHS Colour Chart produced by The Royal Horticultural Society of London, England, with collaboration of the British Colour Council, the observations having been made by me at Arlington Heights, Ill., in the Summer of 1973.

THE PLANT

Origin: Seedling.
Parentage:
- *Seed Parent*—Mons. Jules Elie (unpatented).
- *Pollen Parent*—71D (an unnamed, unpatented "bull" type seedling of Mons. Jules Elie).

Classification: *Paeonia lactiflora.*
Form: Bush.
Shape: Round.
Height: 26 to 28 inches.
Growth: Upright and sturdy with above average strength.
- *Rate of Growth:* Medium.
- *Stem Size:* Large ,about ¾ to 1 inch in diameter at ground level.

- *Branching:* None.

Foliage: Quantity—Abundant with 8 to 12 leaves per stem.
- *Size of Leaf:* 11 to 12 inches long.
- *Shape of Leaf:* Elliptically acute with smooth margins.
- *Texture:* Leathery.
- *Leaflets:* 3 in number, 7 to 8 inches long.
- *Petioles:* 2¾ to 3 inches long.
- *Ribs and Veins:* Pronounced, especially on ventral side.
- *Rachis:* About ½ to ¾ inch long.

THE BUD

Size: Large.
- *Diameter:* About 1¼ to 1½ inches.
- *Depth:* About 1¼ inches.

Form: Ovoid.
Color:
- When sepals first divide—Medium Pink.
- When petals begin to unfurl—Pink, Red Group 55-D.

Sepals: Hooded over bud.
Calyx: Funnel-shaped and large in size.
- *Aspect:* Smooth.
- *Tendency to Split:* None.

THE FLOWER

Blooming Habit: Once annually, in midseason of Spring.
Size of Blossom: Very large.
- *Diameter:* About 9 to 10 inches.
- *Depth:* About 2½ to 3 inches.

Shape of Blossom: Cup-shaped when bloom first opens, changing to full double rose type as bloom matures.
Borne: Singly and terminal, with 3 axillary buds.
Petalage: Petals are many in number.
- *Form:* Double rose type with smooth guard petals.
- *Arrangement:* Imbricated.
- *Color:*
  - Outer petal—Palest Pink, Red Group 56D. Inside petal—Creamy White. Reverse side of petals—Palest Pink, Red Group 56D.
- *Appearance:* Satiny.
- *Petaloids:* None.

Fragrance: Very slight.
Disease Resistance: As observed in nurseries at Arlington Heights and Barrington, Ill., this plant has a high degree of resistance to diseases and insects prevalent in that area.

REPRODUCTIVE ORGANS

Only some rudimentary pistils.

The distinctiveness of this new peony variety resides in the very large size of its ivory and pale pink blossoms which are borne on short, stiff and sturdy stems, the pale pink appearing as a blush in the white of the blossom body. Also, the extra large blossoms are emphasized by an abundance of deep green foliage, all of which provides an attractive presentation of the profusely produced flowers which generally bloom in mid-Spring.

I claim:

1. A new and distinct variety of *Paeonia lactiflora* substantially as herein shown and described, characterized by its extra large pale pink-on-ivory colored double rose type blossoms which are borne on short, stiff and sturdy stems; by the relatively short height of its growth; by its abundance of deep green foliage; and its resistance to disease and insect infestation.

No references cited.

ROBERT E. BAGWILL, Primary Examiner